(12) United States Patent
Terada et al.

(10) Patent No.: US 7,221,502 B2
(45) Date of Patent: *May 22, 2007

(54) MICROSCOPE AND SAMPLE OBSERVATION METHOD

(75) Inventors: Hirotoshi Terada, Hamamatsu (JP); Ikuo Arata, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 39 days.

This patent is subject to a terminal disclaimer.

(21) Appl. No.: 10/804,195

(22) Filed: Mar. 19, 2004

(65) Prior Publication Data

US 2004/0240051 A1   Dec. 2, 2004

(30) Foreign Application Priority Data

Mar. 20, 2003   (JP) ............................. P2003-078819

(51) Int. Cl.
*G02B 21/00*   (2006.01)

(52) U.S. Cl. ...................... 359/381; 359/380; 359/383

(58) Field of Classification Search ........ 359/379–383; 369/13.4, 288
See application file for complete search history.

(56) References Cited

U.S. PATENT DOCUMENTS

| | | | |
|---|---|---|---|
| 5,004,307 A | 4/1991 | Kino et al. | 350/1.2 |
| 5,121,256 A | 6/1992 | Corle et al. | 359/664 |
| 5,125,750 A * | 6/1992 | Corle et al. | 359/819 |
| 5,208,648 A | 5/1993 | Batchelder et al. | 356/237 |
| 5,220,403 A | 6/1993 | Batchelder et al. | 356/345 |
| 5,422,498 A | 6/1995 | Nikawa et al. | 257/48 |

(Continued)

FOREIGN PATENT DOCUMENTS

| | | |
|---|---|---|
| EP | 0 977 192 A1 | 2/2000 |
| JP | 5-80247 | 4/1993 |
| JP | 05-157701 | 6/1993 |
| JP | 06-300824 | 10/1994 |

(Continued)

OTHER PUBLICATIONS

ISTFA, Nov. 2003, "Conference Proceedings from the 29th International Symposium for Testing and Failure Analysis", pp. 325-329.
ISTFA 2003, "Photoemission and OBIRCH Analysis with Solid Immersion Lens (SIL)", pp. 1-20.

*Primary Examiner*—Drew A. Dunn
*Assistant Examiner*—Joshua Pritchett
(74) *Attorney, Agent, or Firm*—Drinkler Biddle & Reath LLP

(57) ABSTRACT

For a semiconductor device S as a sample of an observed object, there are provided an image acquisition part 1 for carrying out observation of the semiconductor device S, and an optical system 2 comprising an objective lens 20. A solid immersion lens (SIL) 3 for magnifying an image of the semiconductor device S is arranged movable between an insertion position where the solid immersion lens includes an optical axis from the semiconductor device S to the objective lens 20 and is in close contact with a surface of the semiconductor device S, and a standby position off the optical axis. Then an image containing reflected light from SIL 3 is acquired with the SIL 3 at the insertion position, and the insertion position of SIL 3 is adjusted by SIL driver 30, with reference to the image. This realizes a semiconductor inspection apparatus (microscope) capable of readily performing observation of the sample necessary for an analysis of microstructure of a semiconductor device or the like, and a semiconductor inspection method (sample observation method) therewith.

9 Claims, 9 Drawing Sheets

U.S. PATENT DOCUMENTS

| | | | |
|---|---|---|---|
| 5,939,709 A | 8/1999 | Ghislain et al. | 250/216 |
| 6,002,792 A | 12/1999 | Oguri et al. | 382/145 |
| 6,226,238 B1* | 5/2001 | Kasono | 369/44.23 |
| 6,441,359 B1* | 8/2002 | Cozier et al. | 250/216 |
| 6,475,398 B2 | 11/2002 | Kitahata | 216/2 |
| 6,594,086 B1 | 7/2003 | Pakdaman et al. | 359/656 |
| 6,600,714 B2 | 7/2003 | Ichimura et al. | 369/275.1 |
| 6,608,359 B2 | 8/2003 | Kitahata | 257/432 |
| 6,621,275 B2 | 9/2003 | Cotton et al. | 324/537 |
| 6,656,029 B2 | 12/2003 | Kitahata | 451/384 |
| 6,687,058 B1 | 2/2004 | Ippolito et al. | 359/656 |
| 6,778,327 B2 | 8/2004 | Pakdaman et al. | |
| 6,828,811 B2 | 12/2004 | Hanson et al. | 324/754 |
| 6,831,782 B2 | 12/2004 | Patton et al. | |
| 6,944,112 B2 | 9/2005 | Challener | |
| 6,961,672 B2 | 11/2005 | Kasapi | 702/182 |
| 2001/0021145 A1* | 9/2001 | Ichimura et al. | 369/43 |
| 2003/0202255 A1 | 10/2003 | Pakdaman et al. | 359/656 |
| 2003/0210057 A1 | 11/2003 | Cotton et al. | 324/501 |
| 2004/0240051 A1 | 12/2004 | Terada et al. | 359/383 |
| 2004/0240074 A1 | 12/2004 | Pakdaman et al. | 359/656 |
| 2005/0002028 A1 | 1/2005 | Kasapi et al. | 356/328 |
| 2005/0030051 A1 | 2/2005 | Hanson et al. | 324/754 |
| 2005/0063046 A1 | 3/2005 | Arata et al. | 359/368 |
| 2005/0094258 A1 | 5/2005 | Tanabe et al. | 359/368 |
| 2005/0094293 A1* | 5/2005 | Tanabe et al. | 359/811 |
| 2005/0190436 A1* | 9/2005 | Terada et al. | 359/381 |
| 2005/0220266 A1* | 10/2005 | Hirsch | 378/43 |

FOREIGN PATENT DOCUMENTS

| | | |
|---|---|---|
| JP | 7-18806 | 3/1995 |
| JP | 07-190946 | 7/1995 |
| JP | 11-003534 | 1/1999 |
| JP | 2002-121930 | 4/2000 |
| JP | 2001-023230 | 1/2001 |
| JP | 2002-189000 | 7/2002 |
| JP | 2002-236087 | 8/2002 |
| JP | 2003-502705 | 1/2003 |
| WO | WO 2004-083930 | 9/2004 |
| WO | WO 2005-083490 | 9/2005 |

* cited by examiner

MICROSCOPE AND SAMPLE OBSERVATION METHOD

BACKGROUND OF THE INVENTION

1. Field of the Invention

The present invention relates to a microscope used for observing a sample such as a semiconductor device, and a sample observation method therewith.

2. Related Background Art

Inspection of semiconductors is implemented using a method of observing a semiconductor device as a sample with a microscope or the like and thereby performing an analysis of failure in a semiconductor device, evaluation of reliability thereof, and so on. The known semiconductor inspection apparatus include an emission microscope, an IR-OBIRCH device, and so on (cf. Japanese Patent Application Laid-Open No. H7-190946 and Japanese Patent Publication No. H7-18806). In recent years, however, the semiconductor devices as inspected objects are being miniaturized more and more, and it is becoming hard for the conventional inspection apparatus using visible light or infrared light, to analyze the microstructure, because of restrictions from the diffraction limit in the optical system.

For this reason, in a case where the microstructure of a semiconductor device is analyzed to detect an abnormal portion in a circuit pattern such as transistors and interconnections formed in the semiconductor device, an abnormality-existing range is first narrowed down to some extent by an inspection apparatus using visible light or infrared light. Then the narrowed-down range is further observed by a method with an observation apparatus such as an electron microscope with higher resolution to detect an abnormal portion in the semiconductor device.

SUMMARY OF THE INVENTION

The method of performing the observation in high resolution with the electron microscope after the inspection with light as described above has a problem that the inspection of semiconductor device requires a great deal of effort and time, for example, because of complicated preparation and installation of the semiconductor device as an inspected object.

On the other hand, a solid immersion lens (SIL) is known as a lens for enlarging an image of an observed object. The SIL is a lens of hemispherical shape, or of hyperhemispherical shape called a Weierstrass sphere. When this SIL is placed in contact with the surface of the observed object, it can increase the numerical aperture NA and magnification and implement observation in high spatial resolution. However, the SIL is a compact lens element about 1 mm in size. For this reason, inspection with the SIL has not been put to practical use yet in the field of the inspection of semiconductor devices, in view of its difficulties in handling, observation control, and so on. This is also the case in observation of samples except for the semiconductor devices.

The present invention has been accomplished in order to solve the above problem, and an object of the invention is to provide a microscope capable of readily carrying out observation of a sample necessary for an analysis of microstructure of a semiconductor device and the like, and a sample observation method therewith.

In order to achieve the above object, a microscope according to the present invention is a microscope for observing a sample, comprising: (1) an optical system comprising an objective lens to which light from the sample is incident, and adapted to guide an image of the sample; (3) a solid immersion lens arranged movable between an insertion position including an optical axis from the sample to the objective lens, and a standby position off the optical axis; (4) solid immersion lens driving means for driving the solid immersion lens between the insertion position and the standby position and for adjusting the insertion position of the solid immersion lens relative to the objective lens; and (5) instructing means for issuing an instruction to adjust the insertion position of the solid immersion lens, with reference to an image containing reflected light from the solid immersion lens.

A sample observation method according to the present invention is a sample observation method of observing a sample, comprising: (a) a first image acquisition step of acquiring an observation image of a sample through an optical system comprising an objective lens to which light from the sample is incident; (b) an observation setting step of setting an observation location in the sample from the observation image; (c) a lens insertion step of moving a solid immersion lens from a standby position off an optical axis from the sample to the objective lens, to an insertion position including the optical axis; (d) a position adjustment step of acquiring an image containing reflected light from the solid immersion lens and adjusting the insertion position of the solid immersion lens relative to the objective lens, with reference to the image; and (e) a second image acquisition step of acquiring an observation image of the sample enlarged by the solid immersion lens, through the solid immersion lens and the optical system.

In the microscope and sample observation method as described above, the microscope is constructed to be able to acquire both the observation image in the normal state without the solid immersion lens between the sample such as a semiconductor device as an observed object, and the objective lens, and the enlarged observation image in the inserted state of the solid immersion lens. Then the image containing the reflected light from the solid immersion lens is acquired in the inserted state of the solid immersion lens, and the position of the solid immersion lens is adjusted with reference to the image.

This configuration permits us to observe the sample in high resolution through the solid immersion lens. By performing the alignment utilizing the observation image in the inserted state of the solid immersion lens, it becomes feasible to efficiently handle the solid immersion lens, in the application to the observation of the sample. The above realizes the microscope capable of readily performing the observation of microstructure of the sample or the like, and the sample observation method therewith. Here the microscope may be configured so that image acquiring means for acquiring an image of the sample is provided with the optical system for guiding the image of the sample.

The above microscope can be applied to a semiconductor inspection apparatus for acquiring an image of a semiconductor device and detecting an abnormal portion thereof, the semiconductor inspection apparatus comprising: image acquiring means for acquiring an image of the semiconductor device as an inspected object; an optical system comprising an objective lens to which light from the semiconductor device is incident, and adapted for guiding the image of the semiconductor device to the image acquiring means; a solid immersion lens arranged movable between an insertion position including an optical axis from the semiconductor device to the objective lens, and a standby position off the optical axis; solid immersion lens driving means for driving the solid immersion lens between the insertion position and the standby position and for adjusting the insertion position of the solid immersion lens relative to the objective lens; and instructing means for issuing an instruction to adjust the insertion position of the solid immersion lens, with reference to the image containing reflected light from the solid immersion lens, which is acquired by the image acquiring means.

The aforementioned sample observation method can be applied to a semiconductor inspection method of acquiring an image of a semiconductor device and detecting an abnormal portion thereof, the semiconductor inspection method comprising: a first image acquisition step of acquiring an observation image of the semiconductor device as an inspected object, through an optical system comprising an objective lens to which light from the semiconductor device is incident; an inspection setting step of setting an inspection location in the semiconductor device from the observation image; a lens insertion step of moving a solid immersion lens from a standby position off an optical axis from the semiconductor device to the objective lens, to an insertion position including the optical axis; a position adjustment step of acquiring an image containing reflected light from the solid immersion lens and adjusting the insertion position of the solid immersion lens relative to the objective lens, with reference to the image; and a second image acquisition step of acquiring an observation image of the semiconductor device enlarged by the solid immersion lens, through the solid immersion lens and the optical system.

In the semiconductor inspection apparatus and inspection method described above, the inspection apparatus is configured so as to be able to acquire both the observation image in the normal state without the solid immersion lens between the semiconductor device as an observed object and the objective lens, and the enlarged observation image in the inserted state of the solid immersion lens. Then the image containing the reflected light from the solid immersion lens is acquired in the inserted state of the solid immersion lens, and the position of the solid immersion lens is adjusted with reference to the image.

This configuration permits us to observe the semiconductor device in high resolution through the solid immersion lens. By performing the alignment utilizing the observation image in the inserted state of the solid immersion lens, it becomes feasible to efficiently handle the solid immersion lens, in the application to the inspection of the semiconductor device. The above realizes the semiconductor inspection apparatus capable of readily performing the inspection of the semiconductor device such as the analysis of microstructure, and the inspection method therewith.

In the above microscope, preferably, the instructing means issues the instruction to adjust the insertion position of the solid immersion lens so that a position of a center of gravity of a reflected light image coincides with an observation location in the sample, with reference to the image containing the reflected light from the solid immersion lens. Similarly, in the sample observation method, preferably, the position adjustment step is to adjust the insertion position of the solid immersion lens so that a position of a center of gravity of a reflected light image coincides with the observation location in the sample, with reference to the image containing the reflected light from the solid immersion lens. This permits us to surely perform the alignment utilizing the observation image in the inserted state of the solid immersion lens. The observation location in the sample is an inspection location in the semiconductor device in the semiconductor inspection apparatus and inspection method.

The microscope may also be configured so that the instructing means issues an instruction to adjust a distance between the objective lens and the sample, along with the adjustment of the insertion position of the solid immersion lens. Similarly, the sample observation method may comprise a distance adjustment step of adjusting a distance between the objective lens and the sample. This permits us to acquire the enlarged observation image of the sample such as the semiconductor device, as an excellent image through the optical system comprising the objective lens, and through the solid immersion lens.

DESCRIPTION OF THE PREFERRED EMBODIMENTS

Figure 1:
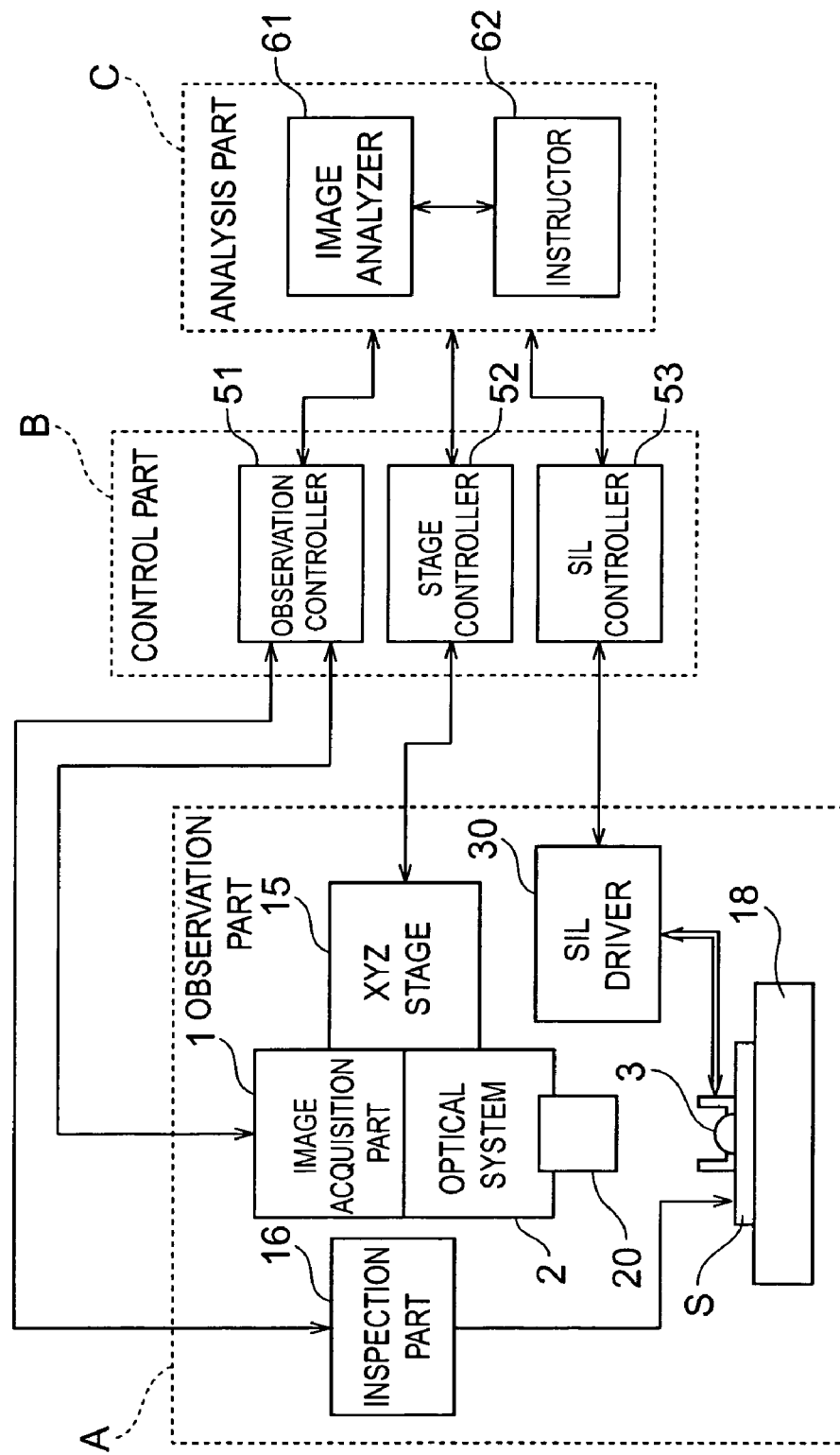
FIG. 1 is a block diagram schematically showing a configuration of an embodiment of the semiconductor inspection apparatus.

Preferred embodiments of the microscope and the sample observation method according to the present invention will be described below in detail with reference to the drawings. In the description of drawings the same elements will be denoted by the same reference symbols, without redundant description. It is also noted that dimensional ratios in the drawings do not always agree with those in the description.

First, a basic configuration of a semiconductor inspection apparatus being a microscope according to the present invention will be described. FIG. 1 is a block diagram schematically showing a configuration of an embodiment of the semiconductor inspection apparatus according to the present invention. The present apparatus is an inspection device adapted for a semiconductor device S, for example, in which a circuit pattern consisting of transistors, interconnections, etc. is formed, as a sample of an observed object (inspected object), and is configured to acquire an image of the semiconductor device S and detect an abnormal portion thereof. Here the microscope and sample observation method according to the present invention are applicable to any cases of general observation of the sample, but the present invention will be described below mainly about the semiconductor inspection apparatus and inspection method as an application example thereof.

The semiconductor inspection apparatus in the present embodiment is comprised of an observation part A for observation of the semiconductor device S, a control part B for control of operations of respective portions in the observation part A, and an analysis part C for processing, instructions, etc. necessary for the inspection of the semiconductor device S. The semiconductor device S as a sample of an inspected object by the present inspection apparatus, i.e., an observed object by the microscope is mounted on a stage 18 in the observation part A.

The observation part A has an image acquisition part 1 housed in a black box (not shown), an optical system 2, and a solid immersion lens (SIL) 3. The image acquisition part 1 is, for example, a means comprised of a photodetector, an image pickup device, or the like and adapted to acquire an image of the semiconductor device S. The optical system 2 for guiding an image of light from the semiconductor device S to the image acquisition part 1 is disposed between the image acquisition part 1, and the semiconductor device S mounted on the stage 18.

The optical system 2 is provided with an objective lens 20 at a predetermined position opposite to the semiconductor device S, to which the light from the semiconductor device S is incident. Light, for example, emerging from or reflected from the semiconductor device S is incident to the objective lens 20 and travels through the optical system 2 including the objective lens 20, to the image acquisition part 1. Then the image acquisition part 1 acquires the image of the semiconductor device S to be used in inspection.

The image acquisition part 1 and the optical system 2 are integrally constructed in a state in which their optical axes are coincident with each other. An XYZ stage 15 is provided for these image acquisition part 1 and optical system 2. This is a configuration capable of achieving alignment and focusing for the semiconductor device S, by optionally moving the image acquisition part 1 and the optical system 2 in the X, Y directions (horizontal directions), and in the Z directions (vertical directions). The alignment and focusing for the semiconductor device S may also be achieved by driving the stage 18 carrying the semiconductor device S.

An inspection part 16 is provided for the semiconductor device S as an inspected object. In the inspection of semiconductor device S, the inspection part 16 performs control of a state of the semiconductor device S and others according to need. There are different methods of controlling the state of the semiconductor device S by the inspection part 16, depending upon specific inspection methods applied to the semiconductor device S; for example, applicable methods include a method of supplying a voltage to a predetermined portion of a circuit pattern formed in the semiconductor device S, a method of irradiating a laser beam as a probe beam to the semiconductor device S, and so on.

Figure 2A:
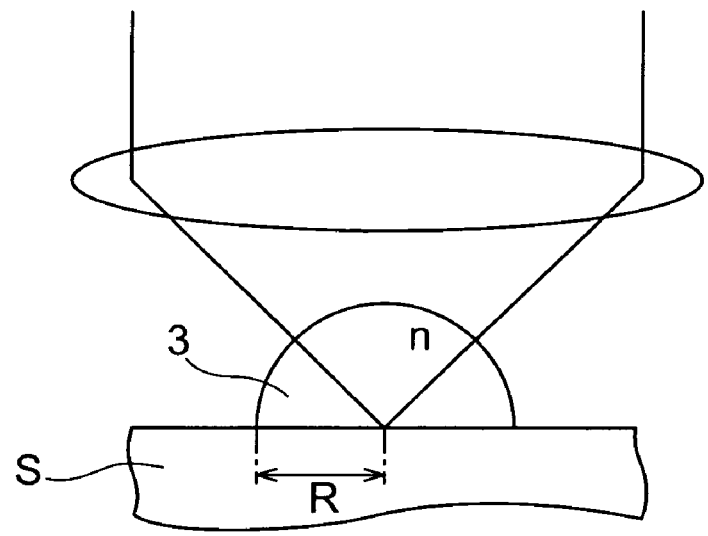
FIG. 2A and FIG. 2B are illustrations showing (A) a solid immersion lens of hemispherical shape and (B) a solid immersion lens of hyperhemispherical shape, respectively.
Figure 2B:
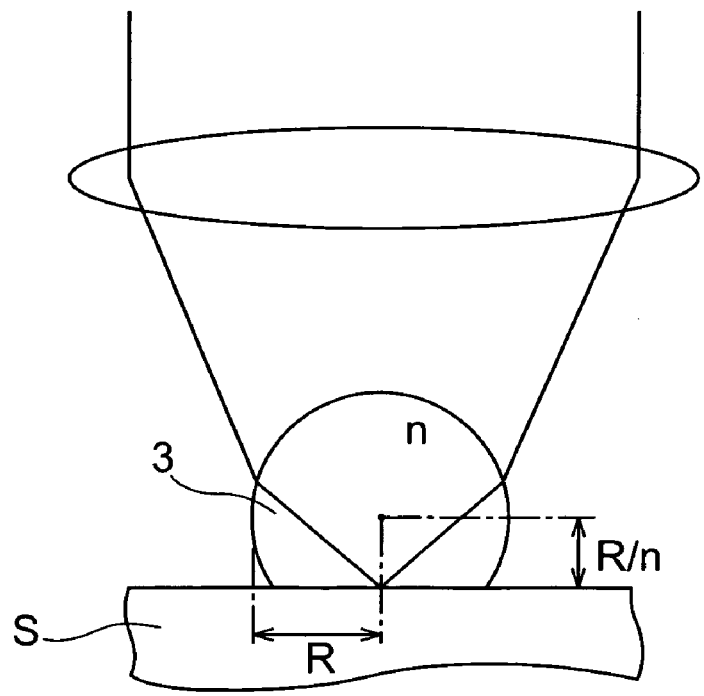

In the present embodiment, SIL 3 is further disposed in this observation part A. FIGS. 2A and 2B are illustrations showing examples of structure and usage of the solid immersion lens (SIL). The SIL 3 is a lens of hemispherical shape, or of hyperhemispherical shape called a Weierstrass sphere, and is placed in close contact with a surface of the semiconductor device S as an observed object, as shown in FIGS. 2A and 2B. Let us suppose here that the radius of SIL 3 is R and the refractive index thereof n.

The lens shape of such SIL 3 is determined according to conditions for nullifying aberration. In the SIL of hemispherical shape, as shown in FIG. 2A, the focal point is at the center of the sphere. In this case, the numerical aperture NA and magnification both increase by n-fold. On the other hand, in the case of the SIL of hyperhemispherical shape, as shown in FIG. 2B, the focal point is located at a position R/n below the center of the sphere. In this case, the numerical aperture NA and magnification both increase by $n^2$-fold. Conceivably, the SIL 3 may also be used under conditions other than those shown in FIGS. 2A and 2B, according to a specific observation condition or the like for the semiconductor device S, e.g., such a condition that the focal point is located at a position between the center of the sphere and the position R/n below the center of the sphere.

In the semiconductor inspection apparatus shown in FIG. 1, the SIL 3 is arranged movable relative to the image acquisition part 1 and optical system 2 and relative to the semiconductor device S mounted on the stage 18. Specifically, the SIL 3 is arranged to be movable between an insertion position at which the SIL 3 is placed so as to include the optical axis from the semiconductor device S to the objective lens 20 and be kept in contact with the semiconductor device S, and a position off the optical axis (a standby position). At the insertion position, the SIL 3 is placed in a state that the plane or convex lower surface of the lens is in close contact with the semiconductor device S. Specific examples of the SIL include such known lenses as plano-convex lenses and bi-convex lenses (e.g., reference should be made to Japanese Patent Application Laid-Open No. H5-157701 and U.S. Pat. No. 6,594,086).

A solid immersion lens driver (SIL driver) 30 is provided for the SIL 3. The SIL driver 30 is a driving means for driving the SIL 3 to move it between the aforementioned insertion position and standby position. The SIL driver 30 finely moves the location of SIL 3 to adjust the insertion position of SIL 3 relative to the objective lens 20 of the optical system 2. In FIG. 1, the SIL 3 is illustrated in a state in which it is placed at the insertion position between the objective lens 20 and the semiconductor device S.

For the observation part A for carrying out the observation and others for inspection of the semiconductor device S, there are provided the control part B and analysis part C.

The control part B has an observation controller 51, a stage controller 52, and an SIL controller 53. The observation controller 51 controls operations of the image acquisition part 1 and inspection part 16, thereby controlling execution of observation of the semiconductor device S carried out in the observation part A, setting of observation conditions, and so on.

The stage controller 52 controls the operation of XYZ stage 15, thereby controlling setting of the observation location in the semiconductor device S by the image acquisition part 1 and optical system 2 as an inspection location in the present inspection apparatus, or alignment thereof, focusing, and so on. The SIL controller 53 controls the operation of SIL driver 30, thereby controlling movement of the SIL 3 between the insertion position and the standby position, or adjustment of the insertion position of SIL 3, or the like.

The analysis part C has an image analyzer 61 and an instructor 62. The image analyzer 61 performs a required analysis process and others for the image acquired by the image acquisition part 1. The instructor 62 gives necessary instructions as to execution of inspection of the semiconductor device S in the observation part A through the control part B, with reference to input contents from an operator, analysis contents by the image analyzer 61, and so on.

Particularly, in the present embodiment, the analysis part C performs necessary processing and instructions about the observation and inspection of the semiconductor device S with the SIL 3, corresponding to the configuration wherein the SIL 3 and SIL driver 30 are placed in the observation part A.

Namely, where the SIL 3 is interposed between the objective lens 20 and the semiconductor device S as a sample, the image acquisition part 1 in the observation part A acquires an image containing reflected light from the SIL 3 in a state in which the SIL 3 is located at the insertion position. In the analysis part C, the image analyzer 61 performs a predetermined analysis, e.g., an operation of determining a position of a center of gravity of a reflected light image in the image containing the reflected light from the SIL 3, which was acquired by the image acquisition part 1. Then the instructor 62 instructs the SIL controller 53 to adjust the insertion position of the SIL 3 so that the position of the center of gravity of the reflected light image coincides with the inspection location (observation location) in the semiconductor device S, with reference to the image containing the reflected light from the SIL 3, which was analyzed by the image analyzer 61.

Figure 3:
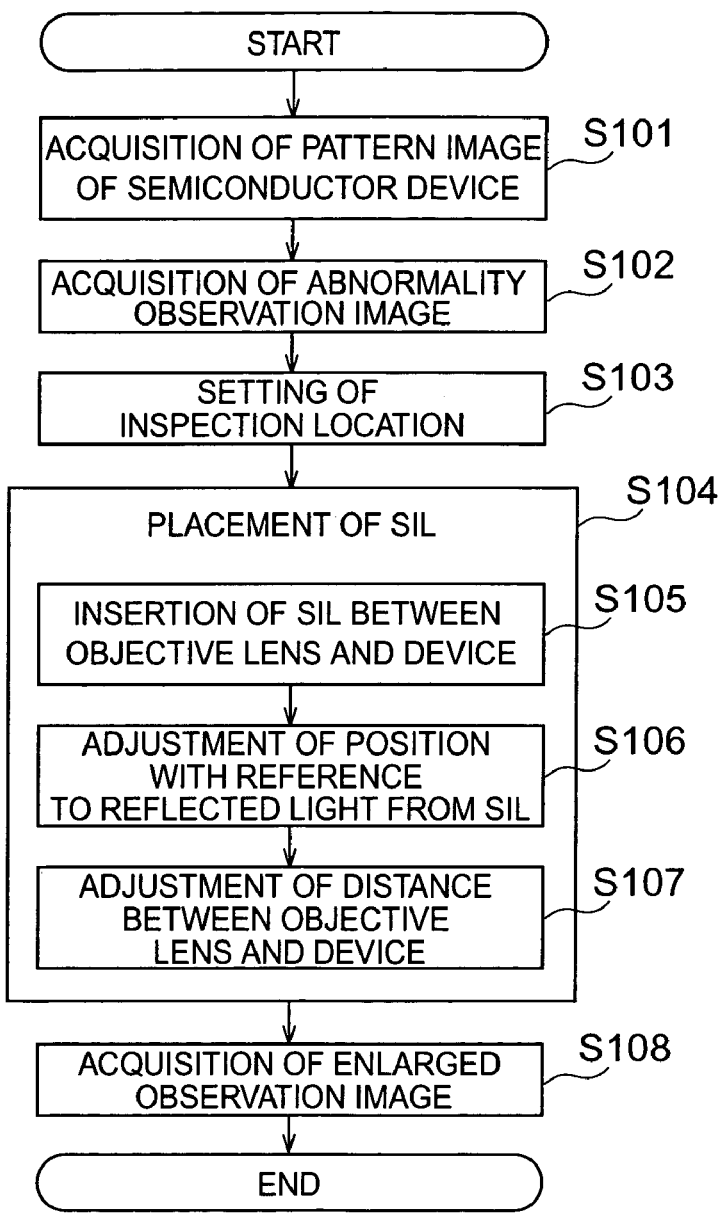
FIG. 3 is a flowchart showing a semiconductor inspection method using the semiconductor inspection apparatus shown in FIG. 1.

A semiconductor inspection method as a sample observation method according to the present invention will be described. FIG. 3 is a flowchart showing the semiconductor inspection method using the semiconductor inspection apparatus shown in FIG. 1.

First, the semiconductor device S as an inspected object is observed in a state in which the SIL 3 is located at the standby position off the optical axis. At this step, the image acquisition part 1 acquires a pattern image of a circuit pattern being an observation image of the semiconductor device S, through the optical system 2 including the objective lens 20 (step S101). The inspection part 16 controls the state of the semiconductor device S to a predetermined state and an abnormality observation image for detection of an abnormal portion in the semiconductor device S is acquired (S102, first image acquisition step).

The next step is to check whether there is an abnormal portion in the semiconductor device S, using the pattern image and abnormality observation image acquired in the image acquisition part 1. If there is an abnormal portion, a position thereof is detected, and the abnormal portion detected is set as an inspection location by the semiconductor inspection apparatus. The inspection location set herein is an observation location in observation of the sample with the microscope (S103, inspection setting step and observation setting step). Then the position of the image acquisition part 1 and optical system 2 is set by the XYZ stage 15 so that the inspection location (observation location) thus set is located at the center of the image acquired by the image acquisition part 1.

Subsequently, setting of the SIL 3 is carried out relative to the inspection location of the semiconductor device S (S104). First, the SIL 3 at the standby position off the optical axis is driven by the SIL driver 30 to move the SIL 3 to the insertion position including the optical axis from the semiconductor device S to the objective lens 20 (S105, lens insertion step).

After the SIL 3 is interposed between the semiconductor device S and the objective lens 20, the insertion position of the SIL 3 is adjusted (S106, position adjustment step). First, an image containing reflected light from the SIL 3 is acquired by the image acquisition part 1. The adjustment of the insertion position of the SIL 3 is carried out using reflected light from the apex of the surface of the SIL 3 in a reflected light image included in this image, as a guide.

Figure 4:
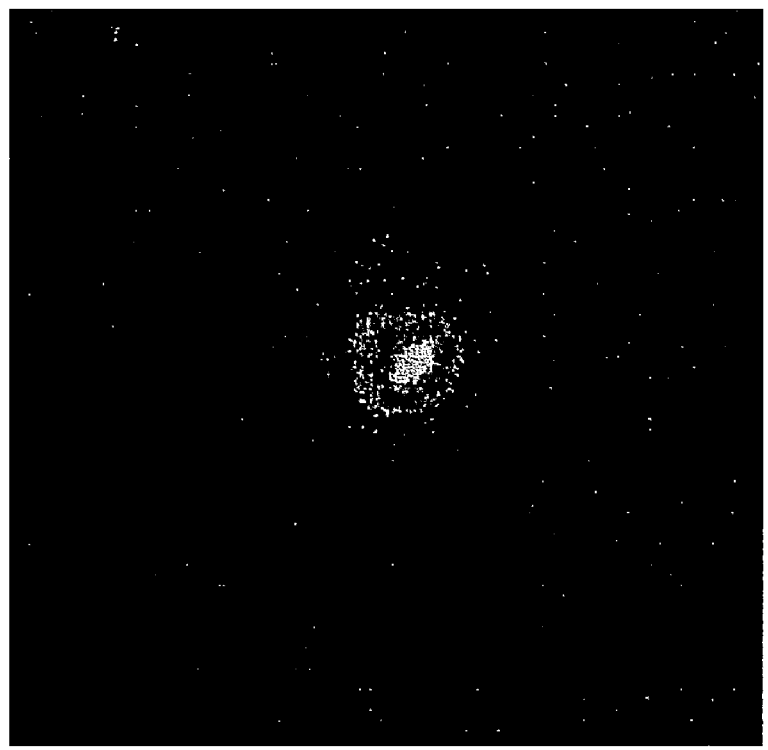
FIG. 4 is a photograph showing an image acquired in an inserted state of a solid immersion lens.

FIG. 4 is a photograph showing an image acquired by the image acquisition part 1 in a state in which the SIL 3 is inserted between the semiconductor device S and the objective lens 20. A bright portion in the center of this photograph corresponds to the reflected light from the apex of the surface of the SIL 3. The image analyzer 61 performs an analysis of the image containing such reflected light from the SIL 3, automatically or based on an instruction from an operator, to determine the position of the center of gravity of the reflected light image. Then the instructor 62 instructs the SIL 3 and SIL driver 30 through the SIL controller 53 to adjust the insertion position of the SIL 3 so that the position of the center of gravity of the reflected light image acquired by the image analyzer 61 coincides with the inspection location in the semiconductor device S. In accordance therewith, the SIL 3 is positioned relative to the semiconductor device S and objective lens 20.

Furthermore, along with the adjustment of the insertion position of the SIL 3 described above, the instructor 62 also instructs the XYZ stage 15 through the stage controller 52 to adjust the distance between the semiconductor device S placed in close contact with the SIL 3, and the objective lens 20 of the optical system 2 (S107, distance adjustment step). This achieves focusing in the inserted state of the SIL 3. Then the image acquisition part 1 acquires an enlarged observation image of the semiconductor device S through the SIL 3 placed on the semiconductor device S and through the optical system 2 including the objective lens 20 (S108, second image acquisition step).

The effects of the semiconductor inspection apparatus and semiconductor inspection method in the present embodiment will be described below.

The semiconductor inspection apparatus shown in FIG. 1 and the semiconductor inspection method shown in FIG. 3 employ the configuration capable of acquiring both the observation image in the normal state without the SIL 3 between the semiconductor device S of the observed object and the objective lens 20 and the enlarged observation image in the inserted state of the SIL 3 by the image acquisition part 1. Then the image containing the reflected light from the SIL 3 is acquired in the inserted state of the SIL 3, and the position of the SIL 3 is adjusted with reference to the image.

This configuration permits one to observe the semiconductor device S as a sample in high resolution through the SIL 3. By performing the alignment utilizing the observation image in the inserted state of the SIL 3, it becomes feasible to efficiently handle the SIL 3, in the application to the inspection of the semiconductor device S (observation of the sample). The above realizes the semiconductor inspection apparatus capable of readily performing the inspection of the semiconductor device S such as the analysis of microstructure or the like, and the inspection method therewith. By the microscope of the above structure and the sample observation method, it becomes feasible to readily perform the observation of the microstructure of the sample or the like.

For the alignment of the SIL 3 using the image containing the reflected light from the SIL 3, specifically, it is preferable to determine the position of the center of gravity of the reflected light image from the SIL 3 and adjust the insertion position of the SIL 3 so that the position of the center of gravity coincides with the inspection location in the semiconductor device S, i.e., with the observation location in the sample, as described above. This enables the alignment of SIL 3 to be achieved with certainty. Possibly, the alignment is achieved by any other alignment method than the above method. For example, the insertion position of the SIL 3 may be adjusted so that the position of the center of gravity of the reflected light image from the SIL 3 coincides with the position of the center of gravity of the inspection location in the semiconductor device S.

Where the inspection of the semiconductor device S is carried out using the SIL 3, it is preferable to locate the inspection location of the semiconductor device S at the center of the image acquired by the image acquisition part 1. This can achieve effective use of the pupil of the objective lens 20 in the observation of the semiconductor device S. Namely, where the SIL 3 is used, the pupil of the objective lens 20 is used only in part, and locations of usage vary according to angles of view. Therefore, the utilization efficiency of light becomes maximum when the SIL 3 is positioned on the optical axis of the objective lens 20. This placement of the SIL 3 can decrease shading occurring in the SIL 3.

In the semiconductor inspection apparatus shown in FIG. 1, the XYZ stage 15 is provided for the image acquisition part 1 and the optical system 2, in order to achieve the alignment and focusing of the image acquisition part 1 and optical system 2 relative to the semiconductor device S. Another possible XYZ stage of this type is an XYZ stage for the stage 18 carrying the semiconductor device S. It is also possible to further provide a θ stage arranged movable in the angular direction.

Figure 5:
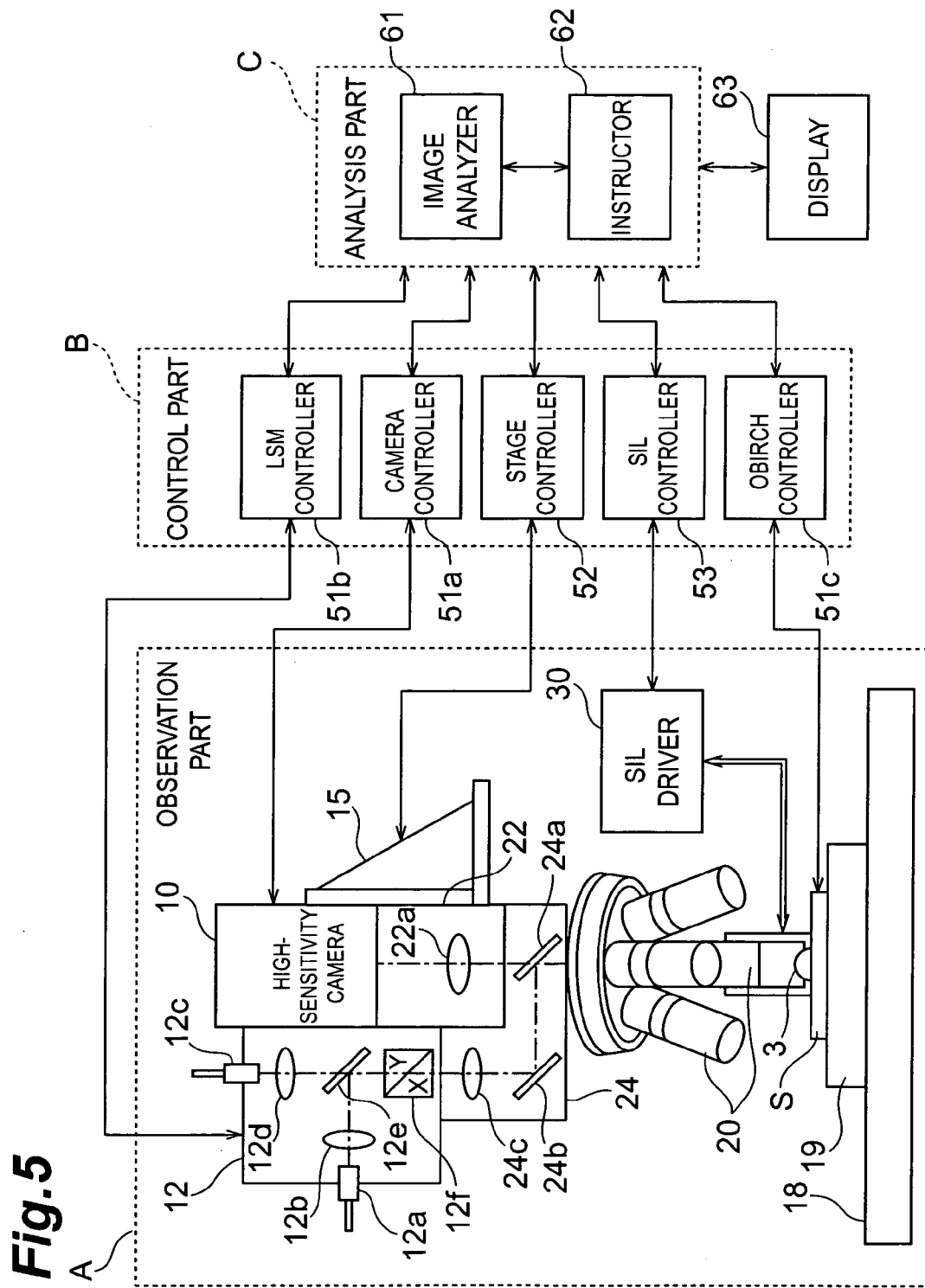
FIG. 5 is a configuration diagram showing another embodiment of the semiconductor inspection apparatus.
Figure 6:
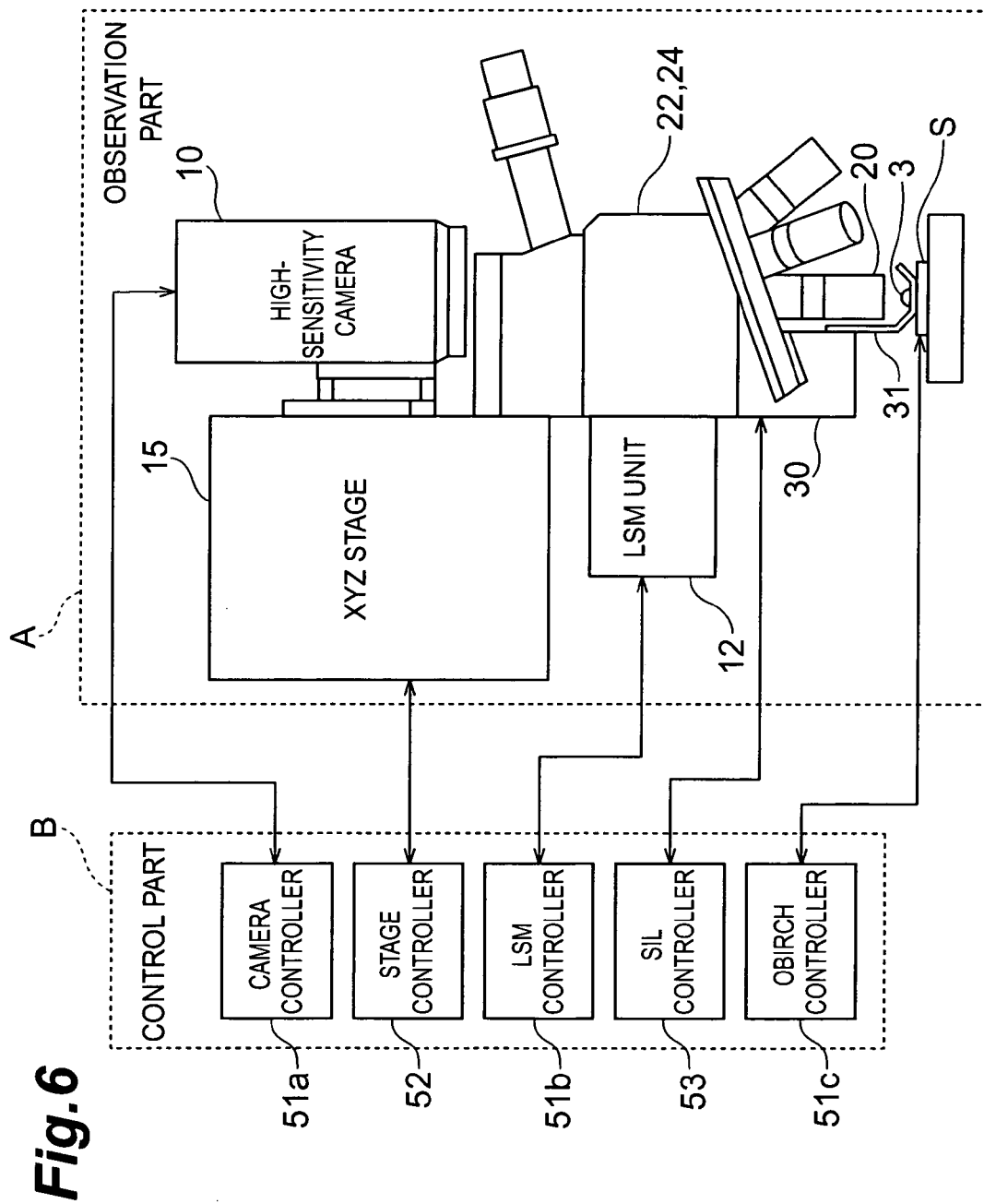
FIG. 6 is a configuration diagram showing a side view of the semiconductor inspection apparatus shown in FIG. 5.

FIG. 5 is a configuration diagram showing another embodiment of the semiconductor inspection apparatus according to the present invention. FIG. 6 is a configuration diagram showing a side view of the semiconductor inspection apparatus shown in FIG. 5. The present embodiment is an example showing a specific configuration of the semiconductor inspection apparatus shown in FIG. 1. In FIG. 6, the analysis part C and others are omitted from the illustration.

The semiconductor inspection apparatus in the present embodiment is provided with an observation part A, a control part B, and an analysis part C. A semiconductor device S as an inspected object is mounted on a stage 18 provided in the observation part A. Furthermore, in the present embodiment, the apparatus is equipped with a test fixture 19 for applying an electric signal necessary for inspection or the like to the semiconductor device S. The semiconductor device S is placed, for example, with its back side facing the objective lens 20.

The observation part A has a high-sensitivity camera 10 set in a black box (not shown), a laser scan optic (LSM: Laser Scanning Microscope) unit 12, optical systems 22, 24, an XYZ stage 15, an SIL 3, and an SIL driver 30.

Among these components, the camera 10 and LSM unit 12 correspond to the image acquisition part 1 in the configuration shown in FIG. 1. The optical systems 22, 24 correspond to the optical system 2. An objective lens 20 is located on the semiconductor device S side of the optical systems 22, 24. In the present embodiment, as shown in FIGS. 5 and 6, a plurality of objective lenses 20 having their respective magnifications different from each other are arranged to be switchable from one to another. The test fixture 19 corresponds to the inspection part 16. The LSM unit 12 also has the function of the inspection part 16 in addition to the function of the image acquisition part 1.

The optical system 22 is a camera optical system for guiding light from the semiconductor device S incident through the objective lens 20, to the camera 10. The camera optical system 22 has an imaging lens 22a for focusing an image magnified at a predetermined magnification by an objective lens 20, on a light receiving surface inside the camera 10. A beam splitter 24a of the optical system 24 is interposed between objective lens 20 and imaging lens 22a. The high-sensitivity camera 10 can be, for example, a cooled CCD camera or the like.

In this configuration, the light from the semiconductor device S is guided through the optical system including the objective lens 20 and the camera optical system 22 to the camera 10. Then the camera 10 picks up an image such as a pattern image of the semiconductor device S. In another configuration, the camera can also picks up an emission image of the semiconductor device S. In this case, light emitted from the semiconductor device S in a voltage applied state by the test fixture 19 is guided through the optical system to the camera 10. Then the camera 10 picks up the emission image of the semiconductor device S to be used as an abnormality observation image. Specific examples of the emission from the semiconductor device S include one due to an abnormal portion based on a defect of the semiconductor device, transient emission with switching operation of a transistor in the semiconductor device, and so on. Furthermore, the acquired image may be an exothermic image based on a defect of device.

The LSM unit 12 has a laser beam introduction optical fiber 12a for irradiating an infrared laser beam, a collimator lens 12b for collimating the laser beam irradiated from the optical fiber 12a, into a parallel beam, a beam splitter 12e for reflecting the laser beam collimated into the parallel beam by the lens 12b, and an XY scanner 12f for moving the laser beam reflected by the beam splitter 12e, in the XY directions to emit the laser beam toward the semiconductor device S.

The LSM unit 12 also has a condenser lens 12d for condensing light having been injected through the XY scanner 12f from the semiconductor device S side and having passed through the beam splitter 12e, and a detection optical fiber 12c for detecting the light condensed by the condenser lens 12d.

The optical system 24 is an LSM unit optical system for guiding light between the semiconductor device S and objective lens 20 and, the XY scanner 12f of the LSM unit 12. The LSM unit optical system 24 has a beam splitter 24a for reflecting part of light having been injected from the semiconductor device S through the objective lens 20, a mirror 24b for changing the optical path of the light reflected by the beam splitter 24a, to the optical path toward the LSM unit 12, and a lens 24c for condensing the light reflected by the mirror 24b.

In this configuration, the infrared laser beam emitted from a laser light source (not shown) and guided through the laser beam introduction optical fiber 12a travels via the lens 12b, beam splitter 12e, XY scanner 12f, optical system 24, and objective lens 20 onto the semiconductor device S and then enters the interior of the semiconductor device S.

Reflectively scattered light from the semiconductor device S with incidence of the incident light reflects a circuit pattern provided in the semiconductor device S. The reflected light from the semiconductor device S travels through the optical path opposite to the incident light to reach the beam splitter 12e, and then passes through the beam splitter 12e. The light through the beam splitter 12e then travels through the lens 12d to enter the detection optical fiber 12c, and is detected by a photodetector coupled to the detection optical fiber 12c.

The intensity of the light detected through the detection optical fiber 12c by the photodetector is the intensity reflecting the circuit pattern provided in the semiconductor device S, as described above. Accordingly, while the infrared laser beam scans the semiconductor device S on the X-Y plane by the XY scanner 12f, a sharp image of the circuit pattern in the semiconductor device S or the like can be picked up.

The observation part A is further provided with the SIL 3. The SIL 3 is arranged movable between the aforementioned insertion position and standby position, relative to the high-sensitivity camera 10, LSM unit 12, optical systems 22, 24, and objective lens 20 and relative to the semiconductor device S mounted on the stage 18. The SIL driver 30 is provided for the SIL 3. The SIL driver 30 is comprised of a lens manipulator having a holder 31 supporting the SIL 3, and is an XYZ driving mechanism for moving the SIL 3 in the X, Y, and Z directions.

The control part B and analysis part C are provided for the observation part A for carrying out the observation and others for inspection of the semiconductor device S.

The control part B has a camera controller 51a, an LSM controller 51b, an OBIRCH controller 51c, a stage controller 52, and an SIL controller 53. Among these, the stage controller 52 and SIL controller 53 are as those described with FIG. 1. The camera controller 51a, LSM controller 51b, and OBIRCH controller 51c correspond to the observation controller 51 in the configuration shown in FIG. 1.

The camera controller 51a and the LSM controller 51b control the operations of the high-sensitivity camera 10 and the LSM unit 12, respectively, thereby controlling the acquisition of an image of semiconductor device S carried out in the observation part A. The OBIRCH controller 51c is provided for acquiring an OBIRCH (Optical Beam Induced Resistance Change) image used in inspection of the semiconductor device S, and extracts an electric current change in the semiconductor device S appearing during a scan with the laser beam.

The analysis part C has an image analyzer 61 and an instructor 62, and is constructed, for example, of a computer or the like. Image information from the camera controller 51a and from the LSM controller 51b is entered through an image capture board provided in the computer of analysis part C. The image analyzer 61 and instructor 62 are as those described with FIG. 1. The image, data, etc. acquired or analyzed by the analysis part C is displayed on the display device 63 coupled to the analysis part C as occasion may demand.

A semiconductor inspection method using the semiconductor inspection apparatus shown in FIGS. 5 and 6 will be schematically described below with reference to the flowchart of FIG. 3.

First, in the normal state in which the SIL 3 is located at the standby position, the semiconductor device S is scanned by the LSM unit 12 to acquire a pattern image of the semiconductor device S (step S101). The next step is to acquire an abnormality observation image used in detection of an abnormal portion in the semiconductor device S (step S102). Specific examples of this abnormality observation image include an OBIRCH image acquired by the OBIRCH controller 51c, an emission image acquired by the camera 10, and so on. These pattern image and abnormality observation image are superimposed on each other, are displayed on the display device 63, etc. as occasion may demand.

The next step is to check an abnormal portion in the semiconductor device S by use of the acquired image and define a detected abnormal portion as an inspection location (S103) and to set the XYZ stage 15 and others so that the inspection location is positioned at the center of the image. Subsequent steps are to carry out the insertion, position adjustment, and distance adjustment of the SIL 3 relative to the inspection location of the semiconductor device S (S104, S105–S107).

Then such an enlarged image as an enlarged pattern image, OBIRCH image, or emission image is acquired through the SIL 3 disposed on the semiconductor device S, and through the objective lens 20 and others (S108). Superposition of the images, the display thereof on the display device 63, etc. are carried out as occasion may demand. In acquisition of an emission image, the stage and others are properly moved so as to match the amount of chromatic aberration caused by the SIL 3, and the magnification is adjusted by software to implement superposition of images.

Figure 7A:
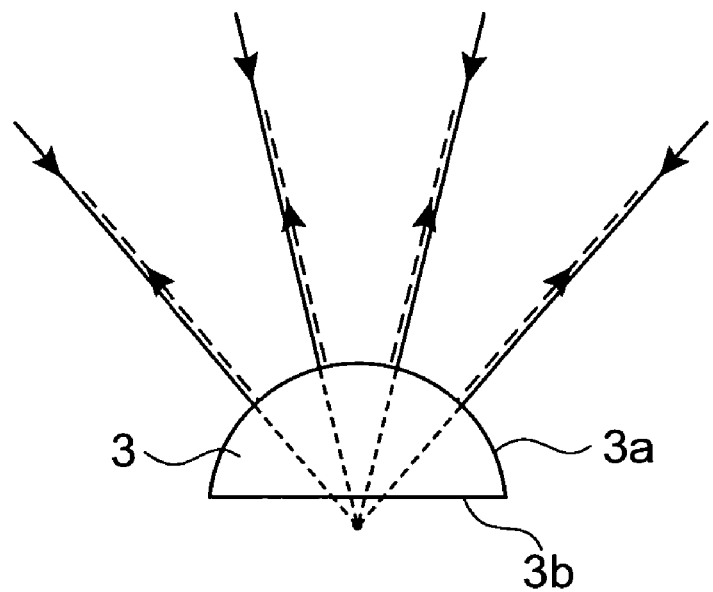
FIG. 7A and FIG. 7B are illustrations showing examples of reflected light patterns in a reflected light image acquired with the solid immersion lens.

The image containing the reflected light from the SIL 3 in the example shown in FIG. 4 will be further described in more detail with reference to FIGS. 7A–9B. Various reflected light patterns as shown in these figures can be contemplated as to the reflected light image acquired for the SIL 3. In FIGS. 7A–9B, incident light to the SIL 3 is indicated by solid lines, and reflected light by dashed lines. In FIGS. 7A and 9B, lines extending toward the center of sphere of the SIL 3 are indicated by dotted lines. Where the optical paths of the incident light and reflected light to and from the SIL 3 are laid over each other, they are illustrated with a shift, for description's sake.

Figure 7B:
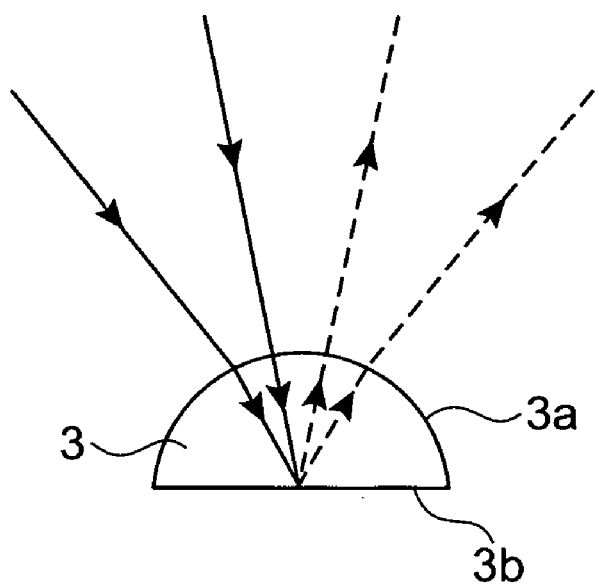

FIG. 7A shows a reflected light pattern in which light incident normally to the spherical top surface 3a of SIL 3 is reflected on the top surface 3a. In this case, the light is focused at one point, so that alignment is easy. Therefore, the alignment can be implemented with high accuracy. FIG. 7B shows a reflected light pattern in which light is reflected at a focal position (center position) on the bottom surface 3b of SIL 3. This is a state of observing the bottom surface 3b of SIL 3. In this case, shading appears significant, and thus the alignment can be implemented by matching a maximum-luminance portion with the center.

Figure 8A:
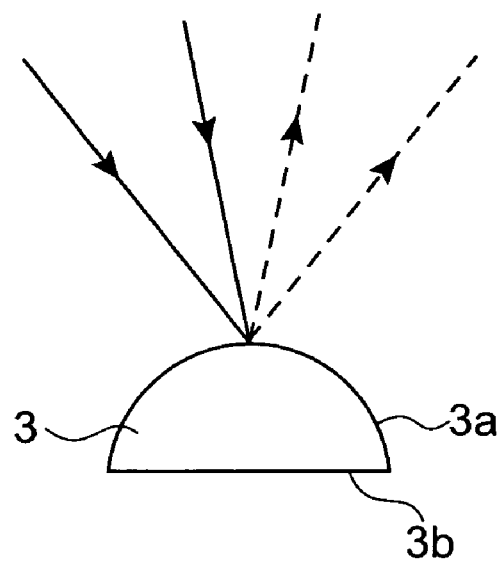
FIG. 8A and FIG. 8B are illustrations showing examples of reflected light patterns in a reflected light image acquired with the solid immersion lens.
Figure 8B:
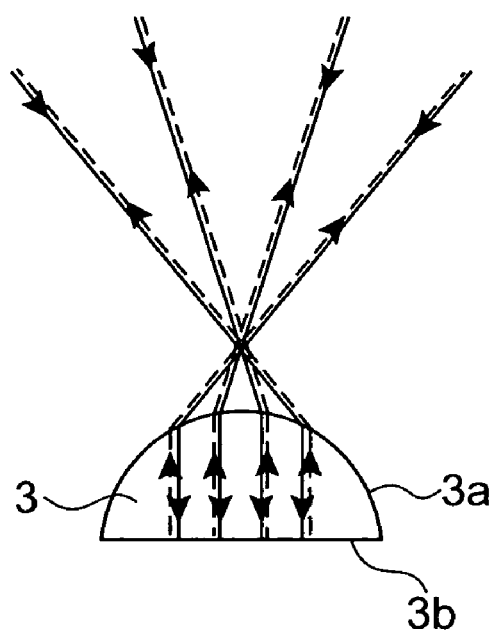

FIG. 8A shows a reflected light pattern in which light is reflected at the focal position (apex position) of the top surface 3a of SIL 3. This is a state of observing the top surface 3a of SIL 3. In this case, shading appears significant, and thus the alignment can be implemented by matching a maximum-luminance portion with the center. FIG. 8B shows a reflected light pattern in which light incident normally to the planar bottom surface 3b of SIL 3 is reflected on the bottom surface 3b. In this case, the light is focused at one point, so that alignment is easy. Therefore, the alignment can be implemented with high accuracy.

Figure 9A:
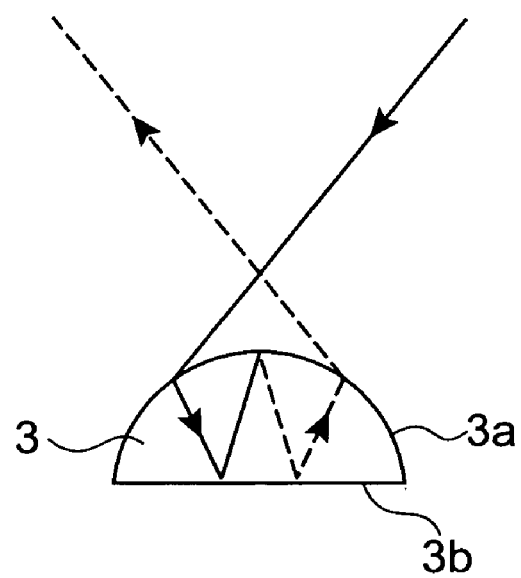
FIG. 9A and FIG. 9B are illustrations showing examples of reflected light patterns in a reflected light image acquired with the solid immersion lens.
Figure 9B:
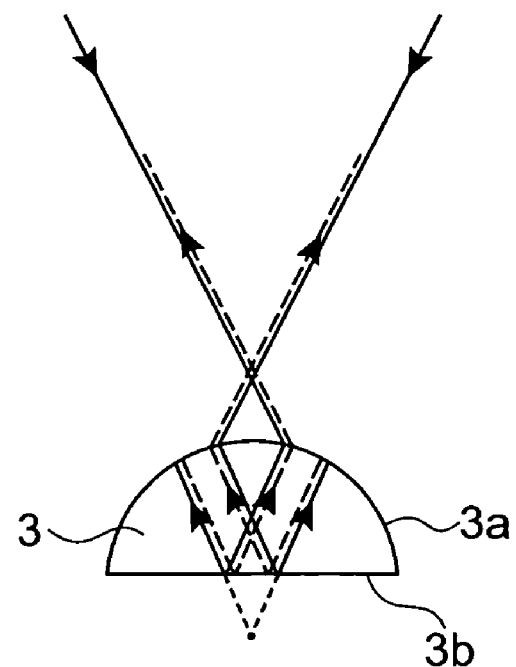

FIG. 9A shows a reflected light pattern in which light is reflected on the bottom surface 3b of SIL 3, at the focal position (apex position) of the top surface 3a, and on the bottom surface 3b. This is a state of observing the top surface 3a of the SIL 3 from the back side. In this case, shading appears significant, and the alignment can be implemented by matching a maximum-luminance portion with the center. FIG. 9B shows a reflected light pattern in which light incident normally to the top surface 3a from the back side via the bottom surface 3b of SIL 3 is reflected on the top surface 3a and is then emitted via the bottom surface 3b. In this case, the light is focused at one point, so that alignment is easy. Therefore, the alignment can be implemented with high accuracy.

The microscopes and sample observation methods according to the present invention are not limited to the above-described embodiments and configuration examples, but can be modified in various ways. For example, as to the specific configurations of the image acquisition part 1, optical system 2, inspection part 16, etc. in the above-stated semiconductor inspection apparatus and as to the specific inspection methods and others for inspection of the semiconductor device S, FIG. 5 and FIG. 6 show just an example of the configurations, but it is also possible to adopt a variety of configurations and inspection methods except for those. Where only the observation is carried out for various devices such as semiconductor devices, the apparatus may be constructed as a device observation apparatus without the inspection part 16. The image acquisition part 1 may also be excluded if not necessary, e.g., where the operator directly observes the image.

Concerning the structure and usage of the SIL, FIGS. 2A and 2B show the state in which the focal point is on the top surface of the semiconductor device S, but in the case of back side observation or the like, the SIL is used so that the focal point is on the back side of the semiconductor device S or at a predetermined position inside the semiconductor device S.

The above embodiments described the semiconductor inspection apparatus and semiconductor inspection methods for an observed object of the semiconductor device, but the present invention can also be applied to cases for samples other than the semiconductor devices, as a microscope and a sample observation method used for observation of a sample. This makes it feasible to readily carry out the observation of microstructure of the sample or the like, in the observation of the sample.

For example, the above-described embodiments used the semiconductor device as a sample of an observed object, and in general, where a variety of devices such as semiconductor devices are used as samples, target devices are not limited to only those using a semiconductor substrate, but may be any observed objects like an integrated circuit using a substrate of glass, a plastic material, or the like, such as a polysilicon thin-film transistor or the like. For example, in the case of a liquid crystal device, the device is fabricated on a glass substrate; in the case of an organic EL device, the device is fabricated on a plastic substrate. Further common samples include bio-related samples using a slide, and others, in addition to the various devices such as the aforementioned semiconductor devices and liquid crystal devices.

The microscopes and sample observation methods according to the present invention, as detailed above, can be applied as microscopes and sample observation methods capable of readily performing the observation of the sample necessary for the analysis of microstructure of the semiconductor device or the like. Namely, the microscope is configured so as to be able to acquire both the observation image in the state without the solid immersion lens between the sample such as the semiconductor device as an observed object, and the objective lens and the enlarged observation image in the inserted state of the solid immersion lens, and is also configured to acquire the image containing the reflected light from the solid immersion lens in the inserted state of the solid immersion lens and adjust the position of the solid immersion lens with reference to the image, whereby it is feasible to perform the observation of the sample in high resolution through the solid immersion lens.

By carrying out the alignment utilizing the observation image in the inserted state of the solid immersion lens, it becomes feasible to efficiently handle the solid immersion lens, in the application to the observation of the sample, for example, such as the inspection of the semiconductor device. The above realizes the microscope capable of readily performing the observation of microstructure of the sample or the like, and the sample observation method therewith. When these microscope and sample observation method are applied to the semiconductor inspection apparatus and inspection method, it is feasible to realize the semiconductor inspection apparatus capable of readily performing the inspection of a semiconductor device such as the analysis of microstructure, and the inspection method therewith.

What is claimed is:

1. A sample observation method of observing a sample, comprising:
    a first image acquisition step of acquiring an observation image of a sample through an optical system comprising an objective lens to which light from the sample is incident;
    an observation setting step of setting an observation location in the sample from the observation image;
    a lens insertion step of moving a solid immersion lens from a standby position off an optical axis from the sample to the objective lens, to an insertion position including the optical axis;
    a position adjustment step of acquiring an image containing reflected light from the solid immersion lens and adjusting the insertion position of the solid immersion lens relative to the objective lens, with reference to the image; and
    a second image acquisition step of acquiring an observation image of the sample enlarged by the solid immersion lens, through the solid immersion lens and the optical system.

2. The sample observation method according to claim 1, wherein the position adjustment step is to adjust the insertion position of the solid immersion lens so that a position of a center of gravity of a reflected light image coincides with the observation location in the sample, with reference to the image containing the reflected light from the solid immersion lens.

3. The sample observation method according to claim 1, comprising a distance adjustment step of adjusting a distance between the objective lens and the sample.

4. A semiconductor inspection method of acquiring an image of a semiconductor device and inspecting the semiconductor device, comprising:
    a first image acquisition step of acquiring an observation image of a semiconductor device through an optical system to which light from the semiconductor device is incident;
    an inspection setting step of setting an inspection location in the semiconductor device from the observation image;
    a lens insertion step of moving a solid immersion lens from a standby position off an optical axis from the semiconductor device to the optical system, to an insertion position including the optical axis;
    a position adjustment step of acquiring an image containing reflected light from the solid immersion lens and adjusting the insertion position of the solid immersion lens relative to the optical system, with reference to the image; and
    a second image acquisition step of acquiring an observation image of the semiconductor device enlarged by the solid immersion lens, through the solid immersion lens and the optical system.

5. The semiconductor inspection method according to claim 4, wherein the position adjustment step is to adjust the insertion position of the solid immersion lens so that a position of a center gravity of a reflected light image coincides with the inspection location in the semiconductor device, with reference to the image containing the reflected light from the solid immersion lens.

6. The semiconductor inspection method according to claim 4, comprising a distance adjustment step of adjusting a distance between the optical system and the semiconductor device.

7. A sample observation method of observing a sample, comprising:

a first image acquisition step of acquiring an observation image of a sample through an optical system to which light from the sample is incident;

an observation setting step of setting an observation location in the sample from the observation image;

a lens arrange step of moving a solid immersion lens from a standby position off an optical axis from the sample to the optical system, to a position including the optical axis; and a second image acquisition step of acquiring an observation image of the sample enlarged by the solid immersion lens, through the solid immersion lens and the optical system.

8. The sample observation method according to claim 7, comprising a distance adjustment step of adjusting a distance between the optical system and the sample.

9. The sample observation method according to claim 7, wherein the sample is a semiconductor device, and the solid immersion lens is placed in close contact with a surface of the semiconductor device.

* * * * *